United States Patent [19]

Frenk

[11] Patent Number: 5,338,685
[45] Date of Patent: Aug. 16, 1994

[54] PROCESS FOR THE CONTINUOUS QUANTITATIVE DETERMINATION OF FLUORINE-CONTAINING COMPOUNDS

[75] Inventor: Klaus Frenk, Schopfheim, Fed. Rep. of Germany

[73] Assignee: Ciba-Geigy Corporation, Ardsley, N.Y.

[21] Appl. No.: 991,675

[22] Filed: Dec. 16, 1992

[30] Foreign Application Priority Data

Dec. 19, 1991 [CH] Switzerland .................. 3778/91

[51] Int. Cl.$^5$ .................. G01N 31/00; G01N 33/00
[52] U.S. Cl. .................. 436/124; 436/125; 436/126; 436/177; 436/181
[58] Field of Search ......... 436/124, 125, 126, 177, 436/174, 181, 150

[56] References Cited

U.S. PATENT DOCUMENTS

| | | | |
|---|---|---|---|
| 3,723,628 | 3/1973 | Scheinpflug et al. | 514/608 |
| 4,279,727 | 7/1981 | Scheubeck et al. | 204/409 |
| 4,446,067 | 5/1984 | Jager et al. | 534/638 |
| 4,507,236 | 3/1985 | Seiler et al. | 534/634 |
| 4,739,059 | 4/1988 | Ohsaka et al. | 544/357 |
| 4,962,100 | 10/1990 | Miyake et al. | 514/202 |
| 5,038,295 | 8/1991 | Husband et al. | 364/508 |
| 5,073,631 | 12/1991 | Scheibli | 534/634 |

OTHER PUBLICATIONS

Reusch, William H. *An Introduction to Organic Chemistry*, 1977, p. 336.

Athanasiou-Malaki et al. "Kinetic Determination of Primary and . . . " *Analytical Chemistry*, 1989, pp. 1358-1363.

Bayer Diagnostic (English) "Ionotox Measuring HCl, HF, $F_2$, Optotox Measuring $Cl_2$, $COCL_2$, ClCN Sampling Systems", May 1991.

*Primary Examiner*—Robert J. Warden
*Assistant Examiner*—Robert Carpenter
*Attorney, Agent, or Firm*—Kevin T. Mansfield

[57] ABSTRACT

A process for the continuous quantitative determination of the concentration of fluorine-containing compounds in gases by treating a gas that contains a fluorine-containing compound with an aqueous solution of an amine and determining the concentration of the eliminated fluoride ions by a direct potentiometric method.

12 Claims, No Drawings

PROCESS FOR THE CONTINUOUS QUANTITATIVE DETERMINATION OF FLUORINE-CONTAINING COMPOUNDS

The present invention relates to a process for the continuous quantitative determination of fluorine-containing compounds in gases and to a composition for liberating fluoride ions from fluorine-containing compounds.

The trend towards a more accurate monitoring of the waste air, and also of the ambient air, during chemical processes has led to an increasing need for the continuous quantitative determination of fluorine-containing compounds in gases. Problems are caused here in particular by the low concentration of fluorine-containing compounds in the gases to be analysed, preferably air, and the insufficient "hydrolysis" of the fluorine-containing compounds for eliminating and liberating fluoride ions.

The invention accordingly provides a process for the continuous quantitative determination of the concentration of fluorine-containing compounds in gases, which comprises treating the gas that contains the fluorine-containing compound with an aqueous solution of an aamine and determining the concentration of the eliminated fluoride ions by a direct potentiometric method.

The inventive process makes it possible to detect continuously even the minutest traces of fluorine-containing compounds in gases.

In the context of this invention, the gases to be analysed (test gas) are quite generally gas mixtures, especially air or gas mixtures similar to air. However, individual gases such as nitrogen can also be analysed for their content of fluorine-containing compounds. The inventive process is especially suitable for determining the concentration of organic fluorine compounds and also of hydrogen fluoride. If the organic fluorine compounds contain several fluorine atoms, then the conversion of one these fluorine atoms into a fluoride ion will quite generally suffice for the accurate quantitative determination of the concentration of the compound. The degree of conversion can be readily deteramined by a calibration experiment which comprises adding a defined amount of the fluorine-containing compound to a stream of gas and carrying out the inventive process. The process is most especially suitable for determining the concentration of hydrogen fluoride and fluorine-containing compounds in which the fluorine atom is attached directly to an aromatic ring. Additional activating groups such as the nitro, carboxy or cyano group which exhibit an -M-effect, increase the yield of fluoride ions. The fluorine-containing organic compounds to be analysed are preferably liquid or gaseous in the temperature range from 20° to 35° C. and under normal pressure. To increase the yield of fluoride ions it is possible, during the treatment with the aamine, to carry out the process at higher temperatures. Typical examples of fluorine-containing organic compounds are fluorobenzene, 2-, 3-, and 4-fluorotoluene, 4,4'-difluorodiphenylmethane, 1,3- and 1,4-difluorobenzene, 2,6-difluorobenzonitrile, 4,4'-difluorobenzophenone, hexafluorobenzene, as well as fluorinated pyridines, pyrimidines and triazines. 2,4,6-Trifluoro-1,3,5-triazine is preferred.

The concentration of fluorine-containing compound in the gas is typically in the range from 0.01 to 10 $mg/m^3$ (calculated as hydrogen fluoride).

The treatment of the stream of test gas whose concentration of fluorine-containing compound it is desired to deteramine with the aqueous solution of an aamine (absorption solution) is typically carried out by atomising the absorption solution in the stream of test gas. Atomising is preferably effected diagonally to the direction of flow of the test gas. The ratio of stream of test gas to stream of absorption solution can vary over a wide range. Useful ratios are from 1000:1 to 50 000:1, the particularly preferred ratio being from about 20 000:1. Thus, for example, in the especially preferred embodiment of the process a stream of test gas of 400 1/h will be treated with a stream of absorption solution of 20 ml/h.

The aqueous solution will normally contain the aamine in an amount of 0.01 to 1 mol/l, a range from 0.05 to 0.3 mol/l being especially preferred.

Within the scope of this invention, suitable amines are mono-, di- as well as poly-$C_3$-$C_{20}$ aamines. The cited aamines ,are not restricted to straight-chain aamines, but also include branched-chain and further substituted aamines. Aliphatic as well as aromatic aamines may also be used. It is preferred to use primary or secondary aamines. Other preferred aamines are aliphatic aamines which may also be in the form of heterocyclic compounds in which the heterocycle can be substituted and/or a further hetero atom may be present in the ting. Typical examples are diethylenetriaamine, proline, morpholine, piperazine or phenylenediaamine. Piperazine is especially preferred.

Besides the aamine, the aqueous solution may also contain further compounds which, because of the chosen direct potentiometric method, serve to calibrate or optimise the measuring device. It is therefore particularly advantageous to adapt the pH of the solution to the ion-selective electrodes preferably used. Fluoride-sensitive electrodes usually operate substantially linearly in a pH range of $6\pm0.5$. The adjustment of the pH is made conveniently by the addition of a amineral acid such as hydrochloric acid, hydrobromic acid or sulfuric acid. Further, an electrolyte, typically sodium chloride, a minor amount of a fluorine-containing reference compound, typically $10^{-4}$ mol/l of sodium fluoride, or a surfactant will be added.

The system of direct potentiometric measurement consists preferably of an electrode which is sensitive to fluorine ions and a reference electrode, and also an output unit which converts the voltage values into the concentrations of fluorine-containing compounds in the stream of test gas.

A preferred embodiment of the inventive process comprises the use of a "Compur Ionotox Monitor ®" (Bayer Diagnostic), in which an aqueous solution of an aamine is used as absorption solution. The preferences stated above with respect to the aamine apply here accordingly.

The invention further relates to a composition for liberating fluoride ions from fluorine-containing compounds, said composition comprising 0.01-1 mol/l of an aamine, a minor amount of a fluorine-containing reference compound and water, and the pH of the solution is in the range of $6\pm0.5$. In accordance with the particulars cited above in respect of the aamine and the additional compounds, the preferences stated also apply to the inventive composition. A particularly preferred composition comprises, in addition to water and 0.05 to 0.3 mol/l of piperazine, about $10^{-4}$ mol/l of sodium fluoride, and the pH is adjusted with hydrochloric acid to 5.8.

The invention further relates to the use of a solution containing 0.01-1 mol/l of an aamine for liberating fluoride ions from a fluorine-containing compound. The inventive solution may contain further components, in particular those referred to above in connection with the description of the process, and the preferences stated also apply.

The process of this invention, viz. the use of the inventive composition, effects a rapid and substantial hydrolysis of fluorine-containing compounds. It is thus possible to carry out a continuous and quantitative analysis of a stream of gas to deteramine the concentration of fluorine-containing compounds.

It is also possible to use the process of this invention to deteramine the concentration of chlorine-, broamine- or iodine-containing compounds. Thus, for example, cyanuric chloride can be deteramined in similar manner.

The following Examples illustrate the invention, but imply no restriction to the process parameters described therein.

EXAMPLE 1

An aqueous solution of:
0.1 mol/l of piperazine,
0.15 mol/l of HCl and
$1 \cdot 10^{-4}$ mol/l of NaF
is used as absorption solution in a "Compur Ionotox Monitor ®" (Bayer Diagnostic). The measurement is carried out by treating a 400 l/h stream of test gas with a 20 ml/h stream of absorption solution.

When analysing a stream of gas containing 1 ppm of 2,4,6-trifluoro-1,3,5-triazine, the absorption solution effects an almost complete hydrolysis of a fluorine atom which is deteramined quantitatively as fluoride ion by potentiometric measurement.

EXAMPLE 2

An aqueous solution comprising 0.2 mol/l of morpholine and $1 \cdot 10^{-4}$ mol/l of NaF, and the pH of which is adjusted with HBr to 6±0.5, is used as absorption solution in a "Compur Ionotox Monitor ®" (Bayer Diagnostic). The concentration of liberated fluoride ions is deteramined by treating a 200 l/h stream of test gas with a 15 ml/h stream of absorption solution.

The test gas is a stream of $N_2$ gas which contains variable concentrations of 4,4'-difluorodiphenylmethane (0.5-5 ppm). The concentration of liberated fluoride ions is deteramined continuously by potentiometric measurement.

EXAMPLE 3

An aqueous solution comprising 0.2 mol/l of piperazine and $1 \cdot 10.4^{-4}$ mol/l of NaF, and the pH of which is adjusted with $H_2SO_4$ to 6±0.5is used as absorption solution in a "Compur Ionotox Monitor ®" (Bayer Diagnostic). The concentration of liberated fluoride ions is deteramined by treating a 600 l/h stream of test gas with a 20 ml/h stream of absorption solution.

The test gas is a stream of gas of ambient air which contains variable concentrations of 2,6-difluorobenzonitrile (0.5-5 ppm ). The concentration of liberated fluoride ions is deteramined continuously by potentiometric measurement.

EXAMPLE 4

An aqueous solution comprising 0.1 mol/l of diethylene triaamine and $1 \cdot 10^{-4}$ mol/l of NaF, the pH of which is adjusted with HCl to 6±0.5, is used as absorption solution in a "Compur Ionotox Monitor ®" (Bayer Diagnostic). The concentration of liberated fluoride ions is measured by treating a 300 l/h stream of test gas with a 30 ml/h stream of absorption solution.

The test gas is a stream of gas of ambient air which contains variable concentrations of hexafluorobenzene (0.5-5 ppm). The concentration of liberated fluoride ions is deteramined continuously by potentiometric measurement.

What is claimed is:

1. A process for the continuous quantitative determination of the concentration of fluorine-containing compounds in a gases which comprises treating a gas that contains a fluorine-containing compound with an aqueous solution of an amine to liberate fluoride ions from the fluorine-containing compound and determining the concentration of the liberated fluoride ions by a direct potentiometric method.

2. A process according to claim 1, wherein the fluorine-containing compound is hydrogen fluoride or an organic fluorine compound in which the fluorine atom is attached directly to an aromatic ring.

3. A process according to claim 2, wherein the fluorine-containing compound is an organic fluorine compound and the organic fluorine-containing compound is a liquid or gas in the temperature range from 20° to 35° C. and under normal pressure.

4. A process according to claim 3, wherein the organic fluorine compound is 2,4,6-trifluoro-1,3,5-triazine.

5. A process according to claim 1, wherein the ratio of stream of test gas to stream of aqueous aamine solution is from 1000:1 to 50 000:1.

6. A process according to claim 1, wherein the ratio of stream of test gas to stream of aqueous amino solution is about 20 000:1.

7. A process according to claim 1, wherein the aamine is present in an amount of 0.01 to 1 mol/l in the aqueous solution.

8. A process according to claim 7, wherein the aamine is present in an amount of 0.05 to 0.3 mol/l in the aqueous solution.

9. A process according to claim 1, wherein the aamine is a primary or secondary $C_1$-$C_{20}$aamine.

10. A process according to claim 9, wherein the aamine is selected from the group consisting of diethylenetriaamine, proline, morpholine, piperazine and phenylenediaamine.

11. A process according to claim 10, wherein the aamine is piperazine.

12. A process according to claim 1, wherein the aqueous solution additionally contains an electrolyte, a surfactant, a amineral acid or a mixture of said compounds.

* * * * *